United States Patent [19]

Burckhardt

[11] Patent Number: 5,237,349
[45] Date of Patent: Aug. 17, 1993

[54] APPARATUS FOR MEASUREMENT OF AN EYE'S RESPONSE TO VISUAL FLICKER

[75] Inventor: Christof W. Burckhardt, Renens, Switzerland

[73] Assignee: Ciposa Microtechniques S.A., Switzerland

[21] Appl. No.: 777,540

[22] PCT Filed: Mar. 27, 1991

[86] PCT No.: PCT/CH91/00080
§ 371 Date: Nov. 26, 1991
§ 102(e) Date: Nov. 26, 1991

[87] PCT Pub. No.: WO91/14399
PCT Pub. Date: Oct. 3, 1991

[30] Foreign Application Priority Data

Mar. 27, 1990 [FR] France .................. 90 04152

[51] Int. Cl.$^5$ .................. A61B 3/10; A61B 3/02
[52] U.S. Cl. .................. 351/205; 351/243
[58] Field of Search .............. 351/205, 221, 243, 211, 351/246, 237, 222; 128/745

[56] References Cited

U.S. PATENT DOCUMENTS 4,142,184 2/1979 Lake .
4,500,844 2/1985 Lisco .
4,567,883 2/1986 Langer et al. .

FOREIGN PATENT DOCUMENTS

88/10088 12/1988 World Int. Prop. O. .

OTHER PUBLICATIONS

Review of Scientific Instruments vol. 51, No. 10, Oct. 1980, New York U.S. pp. 1396–1402; R. E. Gander et al.: "Precise stimulus for the measurement of visual flicker sensitivity" see whole document.
NHK Laboratories Note No. 198, Mar. 1976 Tokyo JP pp. 2–10 Akira Watanabe et al.: "Chromatic spatial sine-wave responses of the human visual system" see whole document.

*Primary Examiner*—Rodney B. Bovernick
*Attorney, Agent, or Firm*—Davis, Bujold & Streck

[57] ABSTRACT

A device for measuring the response of the eye to the flashing of a luminous source comprises a housing (11) containing a source of electrical energy (16), a light-emitting diode (14), an optical system (15) for focusing the light emitted by the source on the retina of the eye and an electronic control device (17). This device is arranged to generate numerical sinusoidal signal with modulation delta, which simplifies the circuit and ensures that the measurements are sufficiently stable.

7 Claims, 2 Drawing Sheets

APPARATUS FOR MEASUREMENT OF AN EYE'S RESPONSE TO VISUAL FLICKER

The present invention concerns a papillometer comprising a flashing luminous source, an optical device for transmitting the light emitted by this source to the eye to be examined, an electronic control device to vary the frequency at which the source flashes and means for measuring eye flickering.

Various types of papillometers, which are devices for measuring the eye's response to the flashing of a light source, are already known. Flickering may be defined as the eye's perception of flashing from a light source. When a light source is made to flash at low frequency with 100% modulation, the eye distinctly perceives the light alternately going on and off. When the flashing frequency of the source increases to a value of the order of 40 Hz, the eye no longer perceives the flashing clearly and the patient's physiological impression is that the light is more intense than it actually is. At an even higher frequency, flickering disappears and gives way to the impression that the light is being continuously emitted. The patient has reached what is known as the fusion threshold, currently called CFF (Critical Flickering Frequency).

If a fixed frequency is maintained and modulation is decreased, the same phenomenon is observed. This phenomenon has been studied by DE LANGE, who proposed submitting the eye to sinusoidal stimulation conforming to the mathematical formula:

$$L = Lo(1 + m\cos\pi ft)$$

shown graphically in FIG. 1.

Frequency f and modulation m may vary independently. The limits for modulation variation are from 0 to 100%, given that it is impossible to create a negative light.

This stimulation makes it possible to plot curves representing the fusion threshold as a function of the frequency and modulation for each eye examined. The general form of these curves is shown in FIG. 2, in which the abscissa shows the logarithm of frequency in Hertz and the ordinate, the logarithm of the inverse of modulation as a percent.

DE LANGE'S curves have three principal applications:

- in the technical realm of television and cinema and in general for any animation projected on a screen, DE LANGE's curves must be taken into account to prevent the viewer's eyes from flickering;
- in physiology, detailed study of DE LANGE's curve with regard to the eye, and particularly the detailed analysis of the small sudden deviations in the curve, aids understanding the information transmission mechanisms inside the retina, especially color perception;
- in medicine, even a gross determination of the DE LANGE curve allows diagnosis of an eye and provides information about the patient's other illnesses or intoxication. Therefore, the papillometer may become a non-invasive diagnostic instrument of general interest, rather than being limited to ophthamological use.

A first mechanical apparatus using polarized filters, rather bulky and costly, was commercialized by the METABO company in Switzerland.

To make this device function independently, use of analog electronics and a light source consisting of light-emitting diodes was attempted. However, these attempts were shown to be relatively inconclusive due to lack of precision and the instability of the light sources over time.

The present invention proposes overcoming the disadvantages described above by achieving a reliably performing papillometer which is nevertheless compact and light.

This goal is achieved by the papillometer according to the invention, characterized in that the control device is designed to generate a numerical sinusoidal signal in delta modulation.

According to a preferred embodiment, the flashing light source is a light-emitting diode.

Preferably the electrical energy source, the light-emitting diode, the optical system for focalizing the light emitted by the source onto the retina of the eye to be examined and the control device are all contained within the same housing.

The electronic control device preferably has a memory in which at least one range of frequencies and at least one range of modulations are stored.

According to a preferred embodiment, the memory system may comprise several storage devices, each corresponding to a range of frequencies, with the stored data defining the control signals for the light source.

The present invention will be better understood with reference to the description of a preferred embodiment and to the attached drawing, in which.

Figure 1:
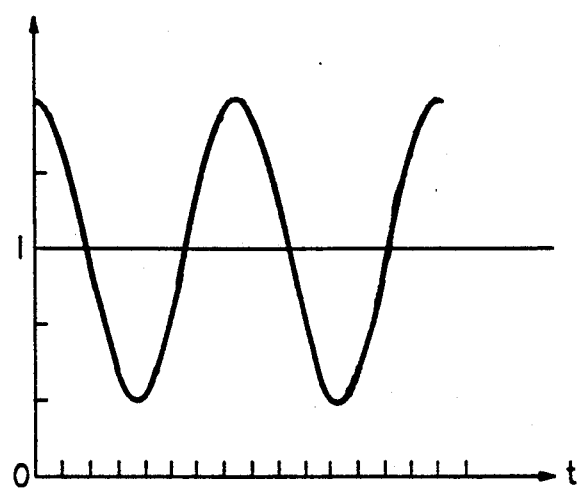
FIG. 1 shows the curve representing the stimulation to which the eye to be examined is submitted.

As stated previously, FIG. 1 represents the sinusoidal curve for stimulation to which the eye to be examined is submitted. This curve conforms to the equation:

$$L = Lo(1 + m\cos 2\pi ft)$$

in which time t is plotted on the abscissa and the value of the stimulation L is plotted on the ordinate, with m being the modulation. For modulation equal to zero, L equals Lo.

Figure 2:
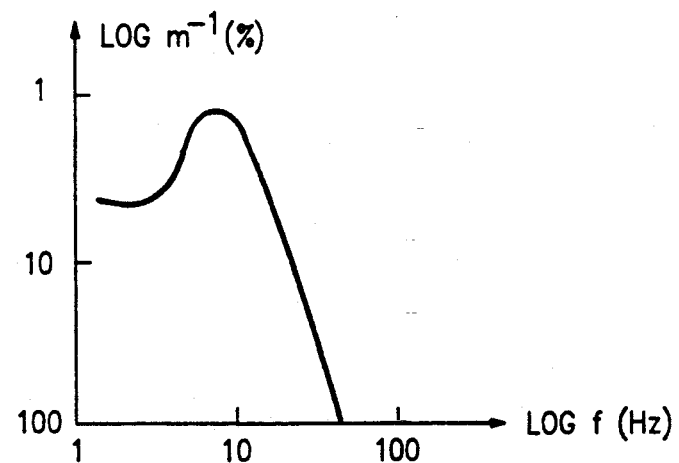
FIG. 2 shows the curve representing the response of the eye submitted to stimulation according to FIG. 1, that is, the DE LANGE curve.

FIG. 2 shows in logarithmic coordinates the general appearance of a DE LANGE curve when the logarithm of the frequency in Hertz is plotted on the abscissa and the logarithm of the inverse of the frequency as a percentage is plotted on the ordinate.

Figure 3:
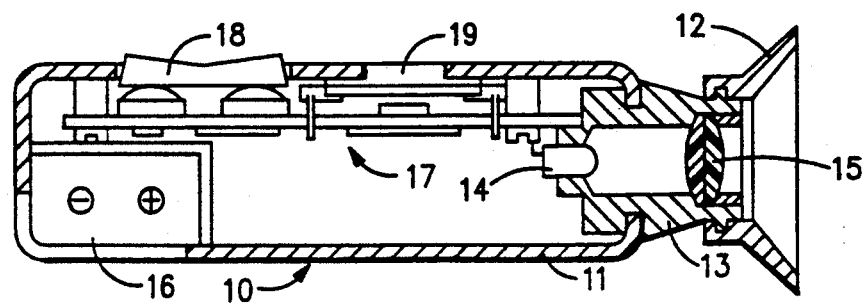
FIG. 3 is a cross-section showing the papillometer according to the invention.

With reference to FIG. 3, the papillometer 10 as shown comprises a generally rectangular housing 11, the back portion of which has an eye piece 12 to be placed in front of the patient's eye. This eye piece is attached to a tubular element 13 integral with housing 11 which contains a light source 14 which may consist, for example, of a photoluminous diode preferably emitting yellow light, as well as an optical focalization system 15.

In addition, housing 11 also contains batteries or a storage cell 16 and an electronic device 17 which will be described in detail below, and which has the specific function of controlling the input to the light source. On the front surface, housing 11 has an on-off switch 18 and two function keys (not shown in this view), as well as a display screen 19, for example, a liquid crystal display.

Figure 4:
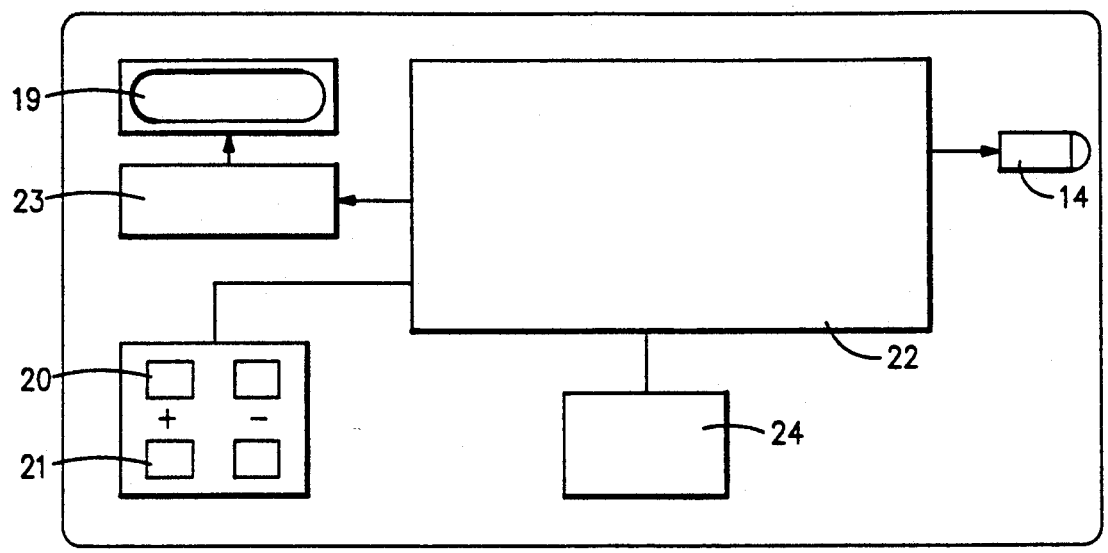
FIG. 4 is a block diagram of the electronic components of the papillometer according to FIG. 3.

FIG. 4 shows the electronic device on the papillometer which has function keys 20 and 21 for respectively increasing and decreasing modulation and frequency.

The function keys are connected to a microprocessor 22, for example, type 6303, which controls the light-emitting diode 14 and which has a second output to a control device 23 for the display registered on screen 19. The electronic device further comprises a memory 24, which is preferably an electrically programmable read-only memory (EPROM).

As stated previously, the light source used is preferably a photoluminous diode emitting yellow light. This diode is directly controlled by a numerical sinusoidal signal in delta modulation. This eliminates the distortions due to the non-linear quality of light-emitting diodes and allows small modulations to be achieved. The spectrum of the modulated signal contains the fundamental and it is the eye which filters the signal. The modulated signal should not, therefore, contain any harmonics between 0 and 100 Hz.

The general principle of delta modulation is knows and was the specific subject of a 1975 publication by PENTAL PRESSILIFE, London - "Delta Modulation Systems" by R. STEELE.

Delta modulation is a differential numerical modulation characterized by extrapolation of order zero and quantification of only one bit so that the only characteristic parameters are frequency of sampling and the step of quantification.

The use of delta modulation allows the circuit to be simplified because it does not require a reactive circuit. Furthermore, for modulations of the order of one per thousand, only delta modulation gives enough stability. Finally, by direct application of delta modulation to the eye, which acts as an integrator, the non-linearities and instabilities influence the average intensity but not the rate of modulation.

The analog signal U(t) which, in this case, is a sinusoid, is compared to the output signal D(t) of the storage cell (16) at a sampling frequency fe.

Figure 5:
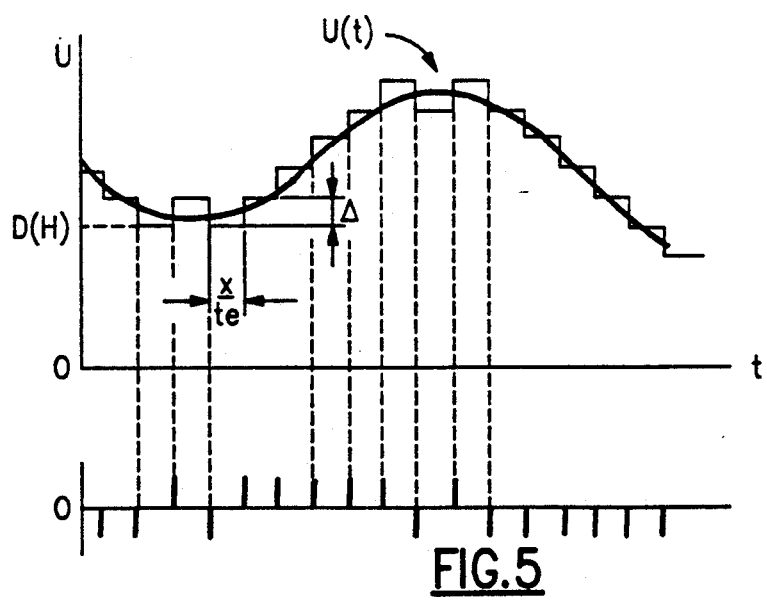
FIG. 5 illustrates the principle of delta modulation providing the input signal for the light source.

After time to, if the analog signal is greater than that of the storage cell, a value of delta sign ($\Delta$) is added to the latter, called the "quantification step", which gives:

$$U(t) \geq D(t) \rightarrow D(to+te) = D(t) + \Delta$$

and in this case, the signal transmitted, ie., the binary unit of information, is equal to 1 (FIG. 5).

Conversely, if the signal U(t) is lower than D(t), the value delta ($\Delta$) is subtracted from D(t), which gives:

$$U(t) \leq D(t) \rightarrow D(t+te) = D(t) - \Delta$$

and in this case, the signal transmitted, i.e., the binary unit of information, is equal to 0 (FIG. 5).

To avoid large distortions, it is necessary for the storage cell output to be able to follow the automatic signal. The slope of sign $\Delta/te$ should be equal to the maximum derivation of U(t).

For the application described, the signal is sinusoidal, thus:

$$|dU/Dt|max = 1 \rightarrow D/te = 1 \rightarrow \Delta = te$$

The signal is directly demodulated by the eye, which acts as a low passage filter.

The choice of sampling is done in the following way: the sinusoidal tables are calculated on a micro-computer. As a result, it is necessary to choose a number of samples per period and not a frequency of sampling. The choice of sampling depends upon the following criteria:
 the greater the number of samples, the greater the signal/noise relationship;
 the maximum frequency of reading and transmitting binary units of information is limited by the microprocessor;
 no harmonic should appear between 0 and 100 Hz..

To obtain a sinusoidal curve showing little distortion and with a good signal/noise relationship, the number of samples per period is high when a low frequency sinusoid is generated (between 2 and 10 Hz approximately 12000 samples per period are obtained), and it is lower for high frequencies.

The sine is not generated by a delta analog-modulation conversion, but is calculated by a microprocessor on the basis of the following general principle:
 a micro-computer program creates a numerical table of sines in delta modulation. This table is then transferred to an EPROM-type memory. The memory is installed in the papillometer where a microprocessor reads the sines in memory and transmits them to the photoluminous diode. There must be a numerical sine in memory for each level of modulation. Modulation variation is not continuous but the memory available, which is for example 64K multiplay, allows storage of more than twenty levels of modulation, which is generally sufficient. In reality, only the half-sine is stored and the micro-processor reconstitutes the missing half period. The memory advantageously comprises several data storage areas in which the frequency ranges are stored.

I claim:

1. An apparatus for measurement of an eye's response to visual flickering, comprising:
 a light source including a light-emitting diode for emitting a flickerable source of light in response to a predetermined sinusoidal control signal,
 optical means positioned adjacent said light-emitting diode for focusing the source of light emitted by said light-emitting diode onto a retina of an eye to be examined,
 an electronic control device comprising a microprocessor having a first output connected to said light-emitting diode for providing said sinusoidal control signal thereto,
 memory means connected to said microprocessor for storing a range of frequencies and a range of modulations,
 a power supply connected to said electronic control device for providing electrical power thereto,
 control means electrically connected to said microprocessor, and including a first function key and a second function key for increasing and decreasing modulation and frequency, respectively, of said sinusoidal control signal, and
 delta-modulation means electrically connected to said microprocessor for causing said microprocessor to generate a digital delta-modulation representation of said sinusoidal control signal.

2. An apparatus according to claim 1, wherein said delta-modulation means comprises comparison means for comparing an analog sinusoidal signal with an output signal of said power supply at a predetermined sampling frequency.

3. An apparatus according to claim 1, wherein said memory means comprises an electrically programmable read-only memory (EPROM).

4. An apparatus according to claim 1, wherein said microprocessor includes a second output for sending an information signal to display means.

5. An apparatus according to claim 1, wherein said apparatus is incorporated into a single housing which contains said light-emitting diode, said optical means and said electronic control device together with said power supply.

6. An apparatus according to claim 1, wherein said memory means comprises a plurality of registers, each corresponding to a range of frequencies, with the stored data determining said control signal.

7. An apparatus for measurement of an eye's response to visual flickering, comprising:

a light-emitting diode for emitting a strobeable source of light in response to a predetermined sinusoidal control signal, optical device positioned adjacent said light-emitting diode for focusing the source of light emitted by said light-emitting diode onto a retina of an eye to be examined, a microprocessor having a first output connected to said light-emitting diode for providing said sinusoidal control signal thereto, a memory connected to said microprocessor for storing a range of frequencies and a range of modulations, a power supply connected to said microprocessor for providing electrical power thereto, at least first and second function keys, electrically connected to said microprocessor, for increasing and decreasing modulation and frequency, respectively, of said sinusoidal control signal, and a delta-modulation mechanism electrically connected to said microprocessor for causing said microprocessor to generate a digital delta-modulation representation of said sinusoidal control signal.

* * * * *